United States Patent
Tafti et al.

(10) Patent No.: US 9,974,642 B2
(45) Date of Patent: May 22, 2018

(54) EXPANDABLE VASCULAR SHEATH AND METHOD OF USE

(71) Applicant: The Regents of the University of California, Oakland, CA (US)

(72) Inventors: Bashir Akhavan Tafti, Oakland, CA (US); Edward W. Lee, Oakland, CA (US); Stephen T. Kee, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 94 days.

(21) Appl. No.: 15/131,104

(22) Filed: Apr. 18, 2016

(65) Prior Publication Data

US 2016/0302908 A1 Oct. 20, 2016

Related U.S. Application Data

(60) Provisional application No. 62/148,249, filed on Apr. 16, 2015.

(51) Int. Cl.
*A61M 29/00* (2006.01)
*A61F 2/01* (2006.01)
*A61B 17/221* (2006.01)
*A61B 17/00* (2006.01)
*A61M 25/00* (2006.01)

(52) U.S. Cl.
CPC ............. *A61F 2/01* (2013.01); *A61B 17/221* (2013.01); *A61B 2017/00867* (2013.01); *A61B 2017/2215* (2013.01); *A61F 2002/011* (2013.01); *A61M 2025/0024* (2013.01)

(58) Field of Classification Search
CPC .... A61F 2/01; A61F 2/95; A61F 2/962; A61F 2/966; A61F 2002/9528; A61F 2002/011; A61M 2025/0024
USPC .................................................. 606/108, 200
See application file for complete search history.

(56) References Cited

U.S. PATENT DOCUMENTS

| | | | |
|---|---|---|---|
| 5,011,488 A | 4/1991 | Ginsburg | |
| 5,643,282 A * | 7/1997 | Kieturakis | A61B 17/3431 606/114 |
| 5,645,083 A * | 7/1997 | Essig | A61B 17/00234 128/898 |
| 5,707,359 A | 1/1998 | Bufalini | |
| 6,159,230 A | 12/2000 | Samuels | |

(Continued)

OTHER PUBLICATIONS

Bard Peripheral Vascular Inc. "Recovery Cone Removal System for use with the G2X Filter, G2 Express Filter, G2 Filter and Recovery Filter Foreign Body Retrievals." PK5014899 Rev. 2, Nov. 2009.

*Primary Examiner* — Melanie Tyson
(74) *Attorney, Agent, or Firm* — Riverside Law LLP

(57) ABSTRACT

An expandable vascular sheath utilizes a set of expandable members such as shape memory alloy wires for expanding its distal end. The wires are slidable along a portion of the sheath's elongate shaft. In certain embodiments, the distal end of the shaft is manufactured with a more pliable and elastic polymer relative to more proximal portions of the elongate shaft, so that as the wires advance into distal portions of the shaft, they expand, causing the distal end opening of the shaft to expand. A method for retrieving a foreign object from a vasculature utilizes a retrieval tool that can be advanced through the expandable vascular sheath.

20 Claims, 4 Drawing Sheets

(56) References Cited

U.S. PATENT DOCUMENTS

| | | | |
|---|---|---|---|
| 8,393,328 B2 * | 3/2013 | Angel | A61M 16/04 128/200.26 |
| 8,414,632 B2 | 4/2013 | Kornkven Volk et al. | |
| 8,470,016 B2 | 6/2013 | Sherburne | |

* cited by examiner

EXPANDABLE VASCULAR SHEATH AND METHOD OF USE

CROSS-REFERENCE TO RELATED APPLICATIONS

This application claims priority to U.S. provisional application No. 62/148,249 filed on Apr. 16, 2015 incorporated herein by reference in its entirety.

BACKGROUND OF THE INVENTION

Medical professionals are commonly required to perform minimally-invasive procedures for the removal of foreign objects from a patient's vasculature. One example of a foreign object that is commonly removed from the vasculature is a vascular filter. Each year in the United States, hundreds of thousands of patients opt for a vascular filter treatment if they are negatively affected by deep vein thrombosis (DVT) and pulmonary embolism (PE). These filters, commonly called inferior vena cava (IVC) filters, capture dislodged blood clots from the inferior vena cava and iliac veins before they can reach the lungs and heart. A typical IVC filter consists of several wire legs arranged in a small conical shape. The filter is inserted into the IVC with the mouth of the cone facing towards the oncoming flow of blood. Barbs on the filter legs secure the filter to the internal walls of the vein, and the conical shape of the legs permit normal blood flow while capturing and holding loose blood clots and emboli.

A retrieval hook for facilitating the removal of the filter from the body is commonly incorporated into filter design. Typically, the retrieval hook is centrally located at the tip of the conical shaped filter. A typical retrieval method and system includes a looped element that can be advanced through a vascular sheath to snare the retrieval hook and drag the filter back into the vascular sheath (see for example Lynch (2012), Modified Loop Snare Technique for the Removal of Bard Recovery, G2, G2 Express, and Eclipse Inferior Vena Cava Filters, *J Vasc Intery Radiol* 2012; 23:687-690.). Other retrieval methods and systems introduce endobronchial forceps through the vascular sheath (see for example Stavropoulos et al. (2008), Embedded Inferior Vena Cava Filter Removal: Use of Endobronchial Forceps, *J Vasc Intery Radiol* 19:1297-1301.). As the filter is pulled up against the walls forming the vascular sheath opening, the filter collapses into the sheath and retracts within the lumen of the sheath. Vascular sheaths vary in geometry, but typically have a tapered or uniform tip. Tapered tips provide ease upon insertion while uniform tips provide a larger opening for entry of the foreign object during retrieval. A dilator having a tapered tip can also be utilized with the Seldinger technique to facilitate advancement of a uniform tip vascular sheath. An appropriate size for the vascular sheath is selected based on multiple factors including the size of the target vessel and the size of the foreign object being removed.

Retrieval of a vascular filter becomes more difficult when migration, misalignment or inadvertent pushing by a retrieval device causes the filter to tilt, positioning the retrieval hook in apposition to the blood vessel wall. When the conical tip of the filter is off-center from the vascular sheath opening, it becomes difficult to smoothly retract and collapse the filter into the vascular sheath opening. Further, a tilted filter may be prone to tissue overgrowth around the retrieval hook if the hook is in contact with the vessel wall. Thus, retrieval mechanisms could be forced to grab a tilted filter at a point other than the retrieval hook, and otherwise drag the tilted filter into the vascular sheath at an angle. As a result of the tilted filter's increased profile, sharp edges and corners of the filter, such as filter joints and barbs could become hooked and snag against the vascular sheath opening, resisting movement of the filter into the opening. This opposition of the filter against the tip of the vascular sheath tip could also damage the vascular sheath, compromising its integrity and risking harm to the patient.

A tilted vascular filter is merely one example of a foreign object that could experience resistance against the smaller diameter of a vascular sheath opening during a retrieval procedure. For example, the same issue could arise during the retrieval of stents, catheter fragments, embolization coils, pacemaker leads, and other types of foreign objects. Certain retrieval systems have been developed to have an opening that expands to facilitate filter retrieval (see for example U.S. Pat. No. 6,156,055 to Ravenscroft). However, these systems are complex, require a compatible filter for use with the recovery device, and may not be useful when the filter is tilted (see for example White et al. (2007), Retrieval of a Wall-Embedded Recovery Inferior Vena Cava Filter Using Rigid Bronchoscopy Forceps, *Seminars in Interventional Radiology*, 24(1), 15-19.).

Thus, what is needed in the art is a vascular sheath that is capable of accommodating the retraction of large profile foreign objects. The vascular sheath should be capable of retrieving a variety of foreign objects including tilted filters, stents, catheter fragments, embolization coils, pacemaker leads, and other types of foreign objects. The vascular sheath should also utilize a design that is simple to manufacture. Further, the vascular sheath should be compatible with a variety of retrieval devices, such as commercially available retrieval snares and endobronchial forceps.

SUMMARY OF THE INVENTION

In one aspect, the invention includes an expandable vascular sheath including an elongate shaft wall and a lumen extending between a proximal end and a distal end along a longitudinal axis and terminating distally in a distal end opening, multiple channels extending longitudinally through the elongate shaft wall, and multiple expanding members slidably disposed within the multiple channels, where the multiple expanding members are configured to expand the distal end opening away from the longitudinal axis responsive to sliding the multiple expanding members in a distal direction.

In another aspect, the invention is a method for retrieving a foreign body from a vessel. The method includes the step of advancing a vascular sheath to a target site within the vessel. The vascular sheath includes an elongate shaft wall and a lumen extending between a proximal end and a distal end along a longitudinal axis and terminating distally in a distal end opening, multiple channels extending longitudinally through the elongate shaft wall, and multiple expanding members slidably disposed within the multiple channels, where the multiple expanding members are configured to expand the distal end opening away from the longitudinal axis responsive to sliding the multiple expanding members in a distal direction. The method further includes the steps of actuating an actuation mechanism to advance the multiple expanding members distally and expand the distal end opening, advancing a foreign body retrieval tool through the lumen, retrieving the foreign body and retracting the foreign body and foreign body retrieval tool proximally through the distal end opening, actuating the actuation mechanism to retract the multiple expanding members proximally and contract the distal end opening, and removing the vascular sheath from the vessel.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 1A shows the expandable vascular sheath in a normal or relaxed unexpanded state, and FIG. 1B shows the expandable vascular sheath in an expanded state.

FIG. 2A is the cross section taken at A-A', FIG. 2B is the cross section taken at B-B', and FIG. 2C is the cross section taken at C-C'.

FIG. 3A shows the expandable vascular sheath advanced to a target position. FIG. 3B shows the expandable vascular sheath opening expanded and a foreign body retrieval tool advanced through the opening. FIG. 3C shows the foreign body retrieval tool grabbing the foreign body. FIG. 3D shows the foreign body retrieval tool retracting the foreign body towards the opening. FIG. 3E shows the foreign body retrieval tool retracting the foreign body into the lumen of the sheath as the opening partially contracts. FIG. 3F shows the foreign body completely retracted within the lumen of the expandable vascular sheath and the opening is fully contracted.

DETAILED DESCRIPTION OF THE INVENTION

Figure 1A:
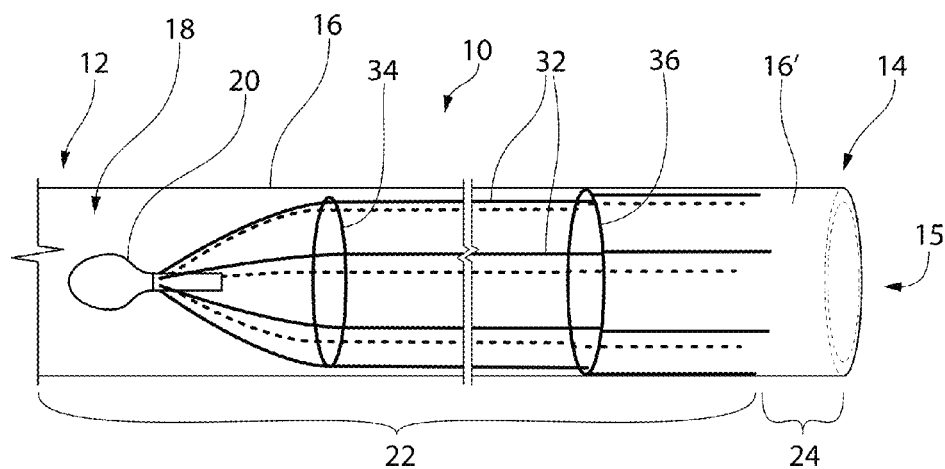
FIGS. 1A and 1B are side cutaway views of an expandable vascular sheath according to an embodiment of the invention.
Figure 1B:
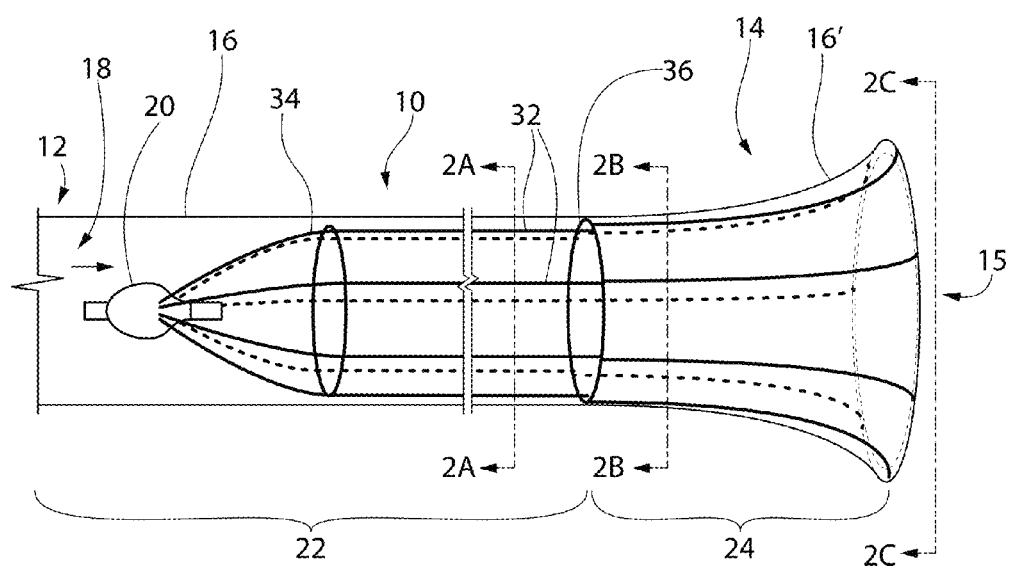

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting. It is to be understood that the figures and descriptions of the present invention have been simplified to illustrate elements that are relevant for a more clear comprehension of the present invention, while eliminating, for the purpose of clarity, many other elements found in expandable vascular sheath systems and methods of retrieving a foreign object from a vessel. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Referring now in detail to the drawings, in which like reference numerals indicate like parts or elements throughout the several views, in various embodiments, presented herein is an expandable vascular sheath system and method for removing a foreign object from a vessel.

Figure 2A:
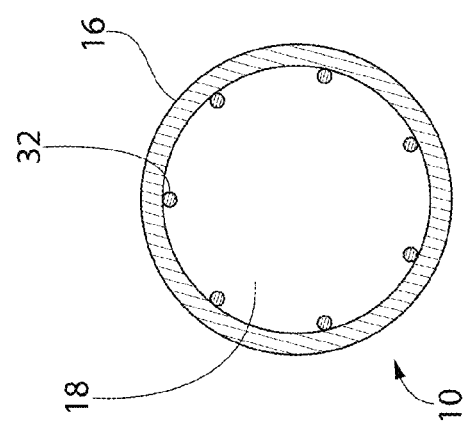
FIGS. 2A-2C are cross-sectional views of the expandable vascular sheath in the expanded state as shown in FIG. 1B.
Figure 2B:
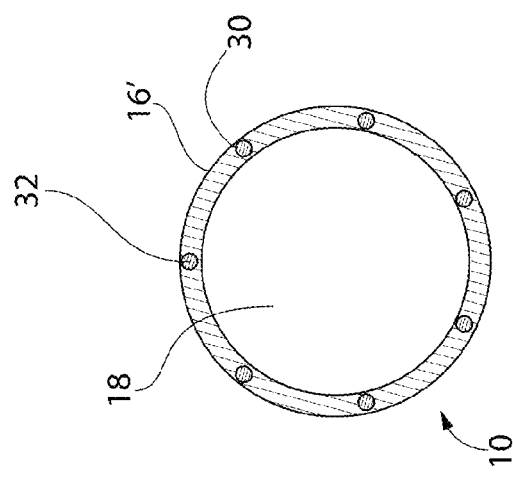

With reference to FIGS. 1A-2B, the expandable vascular sheath 10 has an elongate shaft wall 16 extending between a proximal end 12 and a distal end 14 of the device. The French size of the elongate shaft can vary, depending on the type of object being retrieved and the anatomy of the target vessels. In certain embodiments, the elongate shaft is between 4 French and 12 French. In a preferred embodiments, the elongate shaft is between 5 French and 8 French. The distal end 14 of the shaft wall 16' terminates in a distal end opening 15. The difference between the shaft wall 16 at the first portion 22 and the shaft wall 16' at the second portion 24 will be explained in further detail below (in general, the entire shaft wall including first 22 and second portions 24 is referred to as 16, and in specific instances, the shaft wall specifically at the second portion 24 is referred to as 16'). The shaft wall 16' has a wall thickness that can accommodate channels 30 formed longitudinally through the bulk of the shaft wall 16'. In the exemplary embodiment shown (as illustrated in FIG. 2B), a plurality of channels 30 are formed longitudinally through the bulk of the shaft wall 16' at the second portion 24. The channels 30 are formed to accept shape memory wires 32 such that the wires 32 can slide in a distal and proximal direction through the channels 30. In preferred embodiments, the shape memory wires 32 are a shape memory alloy such as Nitinol. The alloy can be of a composition and geometry to provide adequate rigidity and pushability of the wires, without compromising needed flexibility for navigating the device through the patient's vasculature. In one embodiment, seven wires are used around the circumference of the interior surface of the shaft wall 16. However, it should be appreciated that there is no limitation to the number of wires integrated with the shaft wall 16. For example, at least 3 wires may be used, and in certain embodiments, between 3-50 wires may be used, and preferably between 5-12 wires are used. The wires 32 run through each of the channels 30 and converge in the proximal portion 12 of the lumen 18 onto an actuation mechanism 20. In preferred embodiments, the actuation mechanism 20 has its own lumen to accommodate the insertion of a retrieval tool therethrough. The actuation mechanism 20 may utilize a sliding element that is operably connected outside of the proximal end 12 of the device 10 for manipulation by the medical professional performing the procedure. In alternate embodiments, any other type of mechanical actuation component known in the art (for example, a dialing knob) can be used.

Figure 2C:
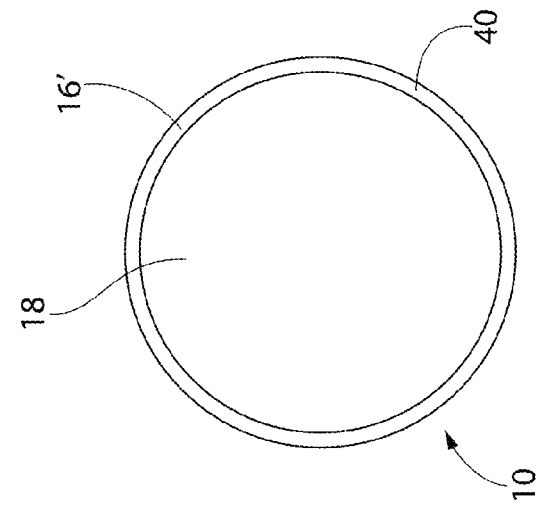

In certain embodiments, the wires 32 run through channels 30 along a minimal length of the shaft wall 16'. Minimizing the coaxial relationship between the wires 32 and corresponding channels 30 can make the device easier to manufacture while minimizing frictional resistance of the wires sliding through the channels. In a preferred embodiment, shown in FIGS. 1A and 1B, the wires 32 open from the actuation mechanism 20 to a first stabilization ring 34 in a conical formation, then extend straight in a distal direction along the inner surface of the shaft wall 16' (see FIG. 2A) to a second stabilization ring 36. The first 34 and second 36 stabilization rings are fixed to the wires 32 such that they move and slide with the wires 32 as a single unit. The stabilization rings 34, 36 help to keep the wires 32 separated and aligned within the lumen 18, further facilitating the pushability of the wires 32. In certain embodiments, between two and eight stabilization rings are used throughout the first portion 22 to keep the wires separated and aligned. In certain embodiments, the device 10 is manufactured and packaged with the distal tips of the wires 32 already inserted within their respective channels 32. Alternatively, a separate alignment guide can be included for inserting the distal tips of the wires 32 into their respective channels 32. The actuation mechanism 20 is configured to limit the proximal sliding range of the wires 32 so that the distal tips of the wires 32 cannot move so far proximally as to slip out of their channels 30 and become misaligned. As shown in FIG. 2C, the distal face 40 of the device 10 is formed as a smooth and contiguous wall, which aids in the smooth insertion of the device into the vasculature. The channels 30 can run distally through the shaft wall 16' so that they terminate just behind the distal face 40, stopping the distal movement of the wires 32. While the wires 32 are pulled back (see FIG. 1A), the distal opening 15 is in an unexpanded state.

Portions of the wires 32 distal of the second stabilization ring 36 are formed with a shape memory that curves away or outwardly from the longitudinal axis of the device 10, thereby forming an expanded diameter and circumference. A first portion 22 of the shaft wall 16 is manufactured with a medical grade polymer that will resist the expansion of the wires 32, keeping them in a compressed and parallel state. The second portion 24 of the shaft wall 16' is manufactured with a medical grade polymer that is highly elastic and pliable, such that as the wires 32 advance distally within their respective channels 30 and towards the distal opening, the distal opening 15 expands to a larger diameter as the wires 32 revert to their relaxed state, and retain their shape memory. In an alternate embodiment, the thickness of the second portion 24 is less than the thickness of the first portion 22 to promote both pliability and a larger distal end opening in the second portion 24. Highly elastic and pliable medical grade polymers can include polymers known in the art, such as urethanes, silastics and latex, and can include polymers with additives for producing softer durometer mixtures. The transition from the first portion 22 material to the second portion 24 can be implemented using any suitable transitioning polymer manufacturing technique known in the art, such as those described in U.S. Pat. No. 4,888,146 to Dandeneau, U.S. Pat. No. 5,542,937 to Chee et al. and U.S. Pat. No. 7,618,411 to Appling.

In alternate embodiments, the distal ends of the wires 32 do not sit within channels 30 at the second portion 24 of the shaft wall 16'. Instead, they can continue to slide and run along the inner surface of the shaft wall 16', pressing outwardly against the inner surface of the second portion 24 to expand the distal opening 15 as they reach the second portion 24. In another alternate embodiment, the relaxed state (e.g. FIG. 1A) of the distal tip can be a tapered tip, so that instead of transitioning from a uniform tip to an expanded tip, the sheath transitions from a tapered tip to an expanded tip, thus aiding in a low resistance insertion and advancement to the target site.

The expandable vascular sheath can be packaged as part of a kit that includes a retrieval tool such as a snare or endobronchial forceps for grabbing and retrieving the foreign object from the vessel. An exemplary method for retrieval of a foreign object is shown in FIGS. 3A-3F. In the example shown, a tilted filter 60 is shown in the IVC 50, with its hook 62 embedded into the caval wall such that tissue overgrowth renders the hook 62 nonfunctional. The expandable vascular sheath 80 is loaded over the retrieval tool 70 and advanced to a target site just above the location of the filter 60 (FIG. 3A). In certain embodiments, the retrieval tool 70 is kitted in a preloaded configuration and coaxially locked in place so that its distal tip sits just inside the distal end of the expandable vascular sheath 80. In this case, the two components are advanced as a single unit to the target site with the retrieval tool 70 acting as a stylet. In other embodiments, the sheath 80 is advanced first using a guidewire and/or a dilator, and the retrieval tool 70 is advanced after the sheath 80 is placed at the target site.

Figure 3C:
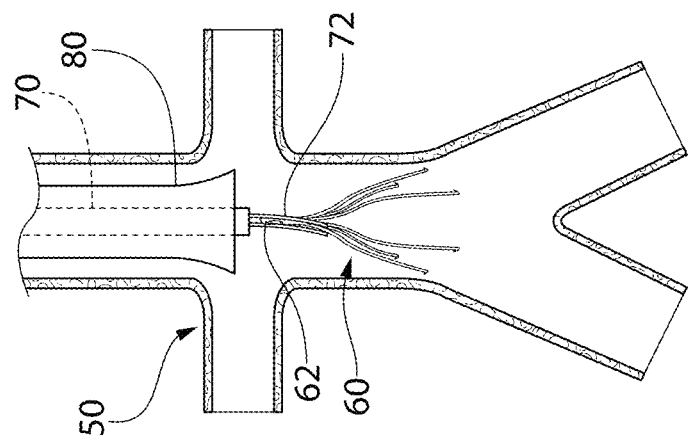
FIGS. 3A-3F are diagrams of an expandable vascular sheath being used to remove a foreign body according to an embodiment of the invention.
Figure 3B:
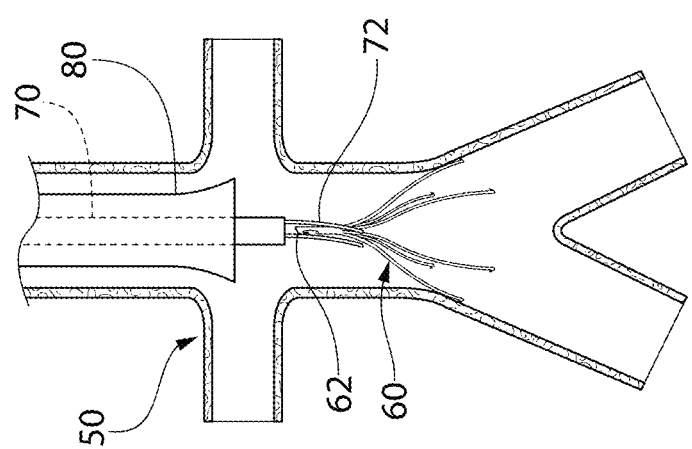
Figure 3A:
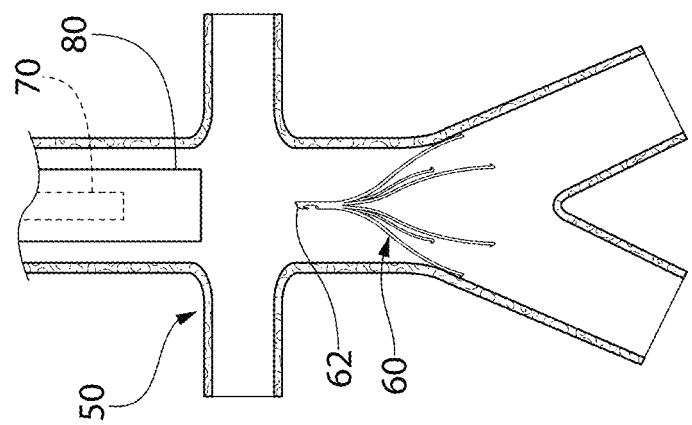
Figure 3D:
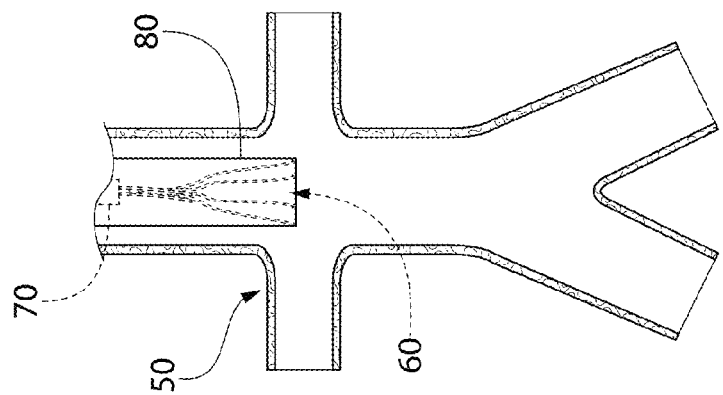
Figure 3E:
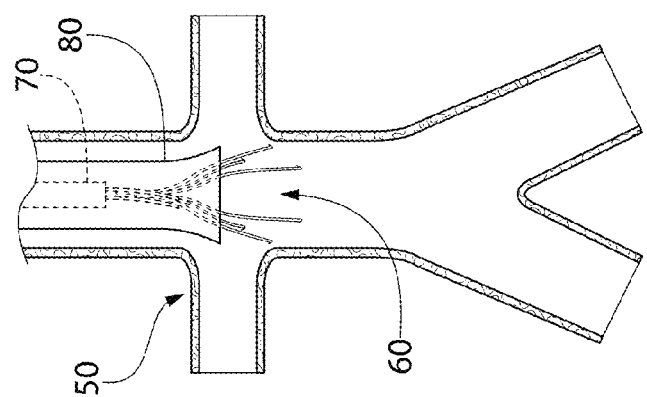
Figure 3F:
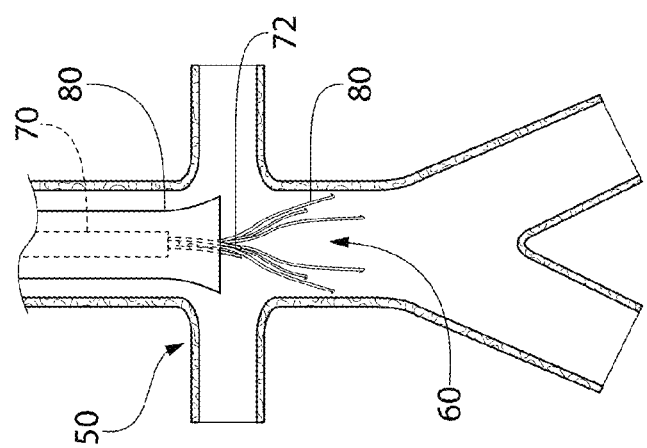

As shown in FIG. 3B, with the retrieval tool 70 and sheath 80 in place, the medical professional pushes the wires 80 forward and the distal opening of the sheath 80 is fully expanded, taking full advantage of available space within the patient's vasculature. In this embodiment, the retrieval tool used is forceps, however, other retrieval tools known in the art can be used, such as a looped or hooked snare. The retrieval tool 70 is then advanced distally towards the filter 60. Since the hook 62 is embedded and the filter 60 is tilted, the grasping elements 72 on the forceps retrieval tool 70 grasp the neck or an accessible leg of the filter 60 (FIG. 3C), below the hook 62, and begins to drag it proximally (FIG. 3D) as the retrieval tool 70 retracts back within the sheath 80. Temporarily expanding the diameter of the sheath's 80 distal opening allows the large profile of the tilted filter 60 to easily enter the sheath 80, without becoming hooked or snagged onto the tip of the sheath 80. Advantageously, when the filter 60 is retracted within the distal end of the sheath 80 as shown in FIG. 3E, the sheath 80 can contract the opening so that it encases the malfunctioning filter 60, facilitating its collapse within the sheath 80 lumen. This technique will help to close the sheath 80 and minimize its opening profile down to its original size for easy removal of the sheath 80 from the vessel 50. The methods and techniques described above are also advantageous for the removal of other types of foreign objects from vessels, including but not limited to stents, catheter fragments, embolization coils and pacemaker leads.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An expandable vascular sheath comprising:
   an elongate shaft wall and a lumen extending between a proximal end and a distal end along a longitudinal axis, the elongate shaft wall terminating distally in a distal end opening, the elongate shaft wall further comprising a first portion and a second portion, wherein the second portion is distal of the first portion, and wherein the second portion comprises the distal end opening;
   a plurality of channels extending longitudinally through the elongate shaft wall; and
   a plurality of expanding members slidably disposed within the plurality of channels;
   wherein the plurality of expanding members are configured to expand the distal end opening away from the longitudinal axis responsive to sliding the plurality of expanding members in a distal direction.

2. The expandable vascular sheath of claim 1, wherein the first portion comprises a first material, the second portion comprises a second material, and the first material is different than the second material.

3. The expandable vascular sheath of claim 2, wherein the first material comprises a first polymer and the second material comprises a second polymer.

4. The expandable vascular sheath of claim 3, wherein the second polymer comprises a higher elasticity than first polymer.

5. The expandable vascular sheath of claim 3, wherein the second polymer comprises a softer durometer than the first polymer.

6. The expandable vascular sheath of claim 1, wherein the plurality of expanding members comprise a shape memory material.

7. The expandable vascular sheath of claim 6, wherein the shape memory material is Nitinol.

8. The expandable sheath of claim 1, wherein the second portion comprises a second wall thickness less than a first wall thickness of the first portion.

9. The expandable vascular sheath of claim 1, wherein the plurality of expanding members and the plurality of channels circumferentially surround the longitudinal axis.

10. The expandable vascular sheath of claim 1, wherein the plurality of expanding members converge onto an actuation mechanism, and wherein the actuation mechanism is configured to advance the plurality of expanding members distally.

11. The expandable vascular sheath of claim 1, wherein the lumen extends between a proximal end opening and the distal end opening, and wherein the lumen is configured to allow a foreign body retrieval tool to advance into the proximal end opening, through the lumen and out of the distal end opening.

12. The expandable vascular sheath of claim 1, wherein the distal end opening is configured to contract towards the longitudinal axis responsive to sliding the plurality of expanding members in a proximal direction.

13. The expandable vascular sheath of claim 1, wherein the plurality of channels terminate proximally of a distal face of the elongate shaft wall.

14. The expandable vascular sheath of claim 13, wherein the distal face of the elongate shaft wall comprises a contiguous surface.

15. A method for retrieving a foreign body from a vessel comprising:
   advancing a vascular sheath to a target site within the vessel, the vascular sheath comprising:
      an elongate shaft wall and a lumen extending between a proximal end and a distal end along a longitudinal axis, the elongate shaft wall terminating distally in a distal end opening,
      a plurality of channels extending longitudinally through the elongate shaft wall, and
      a plurality of expanding members slidably disposed within the plurality of channels,
      wherein the plurality of expanding members are configured to expand the distal end opening away from the longitudinal axis responsive to sliding the plurality of expanding members in a distal direction;
   actuating an actuation mechanism to advance the plurality of expanding members distally and expand the distal end opening;
   advancing a foreign body retrieval tool through the lumen;
   retrieving the foreign body and retracting the foreign body and foreign body retrieval tool proximally through the distal end opening;
   actuating the actuation mechanism to retract the plurality of expanding members proximally and contract the distal end opening; and
   removing the vascular sheath from the vessel.

16. The method of claim 15, wherein the elongate shaft wall further comprises:
   a first portion and a second portion, wherein the second portion is distal of the first portion, wherein the second portion comprises the distal end opening, and wherein the first portion comprises a first material, the second portion comprises a second material, and the first material is different than the second material.

17. The method of claim 16, wherein the first material comprises a first polymer and the second material comprises a second polymer, and wherein the second polymer comprises a higher elasticity than first polymer.

18. The method of claim 15, wherein the plurality of expanding members comprise a shape memory material.

19. The method of claim 15, wherein the plurality of expanding members and the plurality of channels circumferentially surround the longitudinal axis.

20. The method of claim 15, wherein the plurality of channels terminate proximally of a distal face of the elongate shaft wall, and wherein the distal face of the elongate shaft wall comprises a contiguous surface.

* * * * *